US010859855B2

(12) United States Patent
Hernandez-Castaneda et al.

(10) Patent No.: US 10,859,855 B2
(45) Date of Patent: Dec. 8, 2020

(54) METHOD FOR PROVIDING AN OPHTHALMIC LENS TO A WEARER

(71) Applicant: Essilor International, Charenton-le-Pont (FR)

(72) Inventors: Martha Hernandez-Castaneda, Charenton-le-Pont (FR); Nisha Singh, Singapour (SG)

(73) Assignee: Essilor International, Charenton-le-Pont (FR)

( * ) Notice: Subject to any disclaimer, the term of this patent is extended or adjusted under 35 U.S.C. 154(b) by 263 days.

(21) Appl. No.: 16/092,654

(22) PCT Filed: Apr. 11, 2017

(86) PCT No.: PCT/EP2017/058607
§ 371 (c)(1),
(2) Date: Oct. 10, 2018

(87) PCT Pub. No.: WO2017/178452
PCT Pub. Date: Oct. 19, 2017

(65) Prior Publication Data
US 2019/0137784 A1  May 9, 2019

(30) Foreign Application Priority Data

Apr. 15, 2016 (EP) .................................. 16305438

(51) Int. Cl.
*G02C 7/02* (2006.01)
*G02C 7/06* (2006.01)
*A61B 3/04* (2006.01)

(52) U.S. Cl.
CPC ................ *G02C 7/027* (2013.01); *A61B 3/04* (2013.01); *G02C 7/024* (2013.01); *G02C 7/065* (2013.01)

(58) Field of Classification Search
CPC ........ G02C 7/027; G02C 7/065; G02C 7/025; G02C 7/028
See application file for complete search history.

(56) References Cited

U.S. PATENT DOCUMENTS

| 6,142,625 A * | 11/2000 | Sawano | ................. G02C 7/042 351/159.07 |
|---|---|---|---|
| 2004/0085512 A1 | 5/2004 | Roffman et al. | |
| 2006/0209255 A1 | 9/2006 | Donetti et al. | |
| 2015/0219924 A1 * | 8/2015 | Moine | .................... G02C 7/066 351/159.42 |

FOREIGN PATENT DOCUMENTS

| EP | 0 949 529 A2 | 10/1999 |
|---|---|---|
| FR | 2 858 693 A1 | 2/2005 |
| WO | WO 2008/012299 A2 | 1/2008 |
| WO | WO 2012/089234 A1 | 7/2012 |
| WO | WO 2017/013343 A1 | 1/2017 |
| WO | WO 2018/015381 A2 | 1/2018 |

OTHER PUBLICATIONS

International Search Report dated May 15, 2017, in PCT/EP2017/058607 filed Apr. 11, 2017.
P. Allione, et al., "Application of optimization in computer-aided ophthalmic lens design", EUROPTO Conference on Design and Engineering of Optical Systems, SPIE vol. 3737, May 1999, 11 pages.

* cited by examiner

*Primary Examiner* — William R Alexander
*Assistant Examiner* — Ephrem Z Mebrahtu
(74) *Attorney, Agent, or Firm* — Oblon, McClelland, Maier & Neustadt, L.L.P.

(57) ABSTRACT

A method for providing an ophthalmic lens to a wearer including: providing the wearer's astigmatism features measured at a first proximity; providing the wearer's astigmatism features measured at a second proximity, wherein the second proximity is greater than the first proximity; determining customized wearer's astigmatism features based on the combination resulting of linear combinations of the wearer's astigmatism features measured at the first proximity and of the wearer's astigmatism features measured at the second proximity; and applying the customized astigmatism features to the ophthalmic lens.

15 Claims, No Drawings

METHOD FOR PROVIDING AN OPHTHALMIC LENS TO A WEARER

The invention relates generally to the field of vision improvement and more specifically concerns a method for providing an ophthalmic lens to a wearer. The method of the present invention aims improving visual comfort for a wearer.

Conventionally, spectacles lenses are manufactured on request in accordance with specifications intrinsic to individual wearers. Such specifications encompass a medical prescription made by an ophthalmologist or an eye care practitioner.

The medical prescription, also called "wearer's prescription" or "prescription data", refers to one or more data obtained for the wearer and indicating for at least an eye, preferably for each eye, how to correct the ametropia of each eye for the wearer; the medical prescription usually comprises a prescribed sphere $SPH_p$, a prescribed astigmatism value $CYL_p$ associated with a prescribed axis $AXIS_p$, suitable for correcting the ametropia of each eye for the wearer. When the wearer is a presbyopic wearer, the medical prescription may also comprise a prescribed addition $ADD_p$ for correcting the presbyopia of each of the eyes of said wearer.

SPH is an abbreviation for spherical correction. This corrects refractive error of the eye with a single convergent or divergent refractive power in all meridians.

CYL is an abbreviation for cylindrical correction. This corrects astigmatic refractive error of the eye by adding or subtracting power cylindrically in a meridian specified by the prescribed axis.

AXIS is present only if there is a non nil value for CYL. This indicates the angle in degrees of one of two major meridians the prescribed cylindrical power is in. Which major meridian is referenced is indicated by the cylindrical correction being in plus or minus notation.

Both cylindrical correction and axis refer to correction of the astigmatism of an eye.

Astigmatism is an optical defect in which vision is blurred due to the inability of the optics of the eye to focus a point object into a sharp focused image on the retina. Astigmatism may be due to combination of external (corneal surface) and internal (posterior corneal surface, human lens, fluids, retina, and eye-brain interface) optical properties of an eye. Uncorrected astigmatism causes eyestrain and headaches, especially after reading or other prolonged visual tasks.

According to common prescription methods, an ophthalmologist or an eye care practitioner measures the prescribed sphere $SPH_p$, the prescribed astigmatism value $CYL_p$ and the prescribed axis $AXIS_p$ when the wearer is looking in a far vision gaze direction.

The inventors have noticed that wearers may complain of visual fatigue when wearing ophthalmic lenses provided on the basis of such common prescription methods; they have identified that it may be due to prolonged near vision work and that said visual fatigue may be lowered when taking into account astigmatism correction for near vision that may be different from astigmatism correction for far vision.

A problem that the invention aims to solve is thus to enhance the wearer's visual comfort, namely when the astigmatism correction of the wearer is different when measured for different viewing distances. On the other hand, in prior known solutions, some progressive lenses are designed to take into account the change in astigmatism (CYL and AXIS) between different viewing distances. However, manufacture of such lenses is complex because the CYL and AXIS change between different viewing distances would require using free form surfaces to obtain such lens product. Thus another objective of the invention is to provide a simple solution for providing a lens which can still enhance the wearer's visual comfort taking into account the change in astigmatism.

Another problem related to known solutions is that they provide a progressive design to the wearer even if the wearer is not presbyopic. This can lead to low acceptance of this kind of optical design since non presbyopic wearers are used to wear single vision lenses. Another problem also related to known solutions, is that even for presbyopic wearer that are used to wear progressive design lenses, the progression of cylinder axis or modulus between far and near vision zone can induce additional distortions that would lead also to low acceptance of the lens.

For this purpose, a subject of the invention is a method for providing an ophthalmic lens both for presbyopic or not presbyopic wearer comprising the steps of:

Providing wearer's astigmatism features measured at a first proximity Prox1, said wearer's astigmatism features comprising a modulus of astigmatism AST_MOD1 and an axis of astigmatism AST_AX1;

Providing wearer's astigmatism features measured at a second proximity Prox2, said wearer's astigmatism features comprising a modulus of astigmatism AST_MOD2 and an axis of astigmatism AST_AX2, wherein the second proximity Prox2 is greater than the first proximity Prox1;

Determining customized astigmatism features (AST_MOD_C, AST_AX_C) thanks to the combination of the wearer's astigmatism features measured at the first proximity Prox1 (AST_MOD1, AST_AX1) and of the wearer's astigmatism features measured at the second proximity Prox2 (AST_MOD2, AST_AX2);

Applying said customized astigmatism features (AST_MOD_C, AST_AX_C) to the ophthalmic lens so as to provide the wearer astigmatism correction (AST_MOD_C, AST_AX_C) for both the first proximity Prox1 and second proximity Prox2;

wherein the combination of the wearer's astigmatism features measured at the first proximity Prox1 and of the wearer's astigmatism features measured at the second proximity Prox2 results of linear combinations where:

AST_MOD_$C=a\cdot$AST_MOD1$+b\cdot$AST_MOD2;
AST_AX_$C=c\cdot$AST_AX1$+d\cdot$AST_AX2;

Parameters a, b, c and d are positive or nil values, each being equal or less to 1; parameter a value is different from 1 and/or parameter c value is different from 1; a+b=1 and c+d=1.

Proximity is the inverse of the distance between an object point and the front surface of a lens, on corresponding light ray. Accordingly a second proximity Prox2, which is greater than a first proximity Prox1, relates to a viewing distance which is nearer than the one corresponding to said first proximity Prox1.

The inventors have discovered that providing an ophthalmic lens to a wearer thanks to here above method is suitable for enhancing his visual comfort, namely when performing long visual tasks at a distance corresponding to the second proximity Prox2. In the meantime, as customized astigmatism features (AST_MOD_C, AST_AX_C) are applied to the ophthalmic lens for both the first proximity Prox1 and second proximity Prox2, the manufacture of a complex lens with free form surfaces can be avoided.

According to different embodiments of the present invention, that may be combined:

the method further comprises the step of providing the wearer's prescribed mean refractive power for the first proximity Prox1;

the lens is an ophthalmic single vision lens, and said customized astigmatism features (AST_MOD_C, AST_AX_C) are applied to the whole surface of the lens; according to another embodiment, the lens is an ophthalmic progressive addition lens, and said customized astigmatism features (AST_MOD_C, AST_AX_C) are applied to the meridian line of a target lens used to calculate by computer means the ophthalmic lens for the wearer the by performing an optimization with said target lens;

the first proximity and the second proximity (Prox1, Prox2) are chosen within the list consisting of (Prox1=Far vision proximity, Prox2=Near vision proximity), (Prox1=Far vision proximity, Prox2=Intermediate vision proximity), (Prox1=Intermediate vision proximity, Prox2=Near vision proximity). According to an embodiment, the first proximity is the far vision proximity; According to an embodiment, the second proximity is the near vision proximity;

the values of previous parameters a, b, c and d are chosen according to a set of rules as a function of the wearer's needs;

the wearer's needs refer to far vision and to near and/or intermediate vision(s) visual tasks and the values of previous parameters a, b, c and d are chosen according to following rules:

$a=c=0$ and $b=d=1$, when abs(AST_MOD2−AST_MOD1)<0.5 Diopter and when abs(AST_AX2−AST_AX1)<5°;

$a=d=0$ and $c=b=1$, when abs(AST_MOD2−AST_MOD1)<0.5 Diopter and when abs(AST_AX2−AST_AX1)≥5°;

$b=c=0$ and $a=d=1$, when abs(AST_MOD2−AST_MOD1)≥0.5 Diopter and when abs(AST_AX2−AST_AX1)<5°;

a, b, c and d values are each a value equal or less to $\frac{2}{3}$ and are each a value equal or greater to $\frac{1}{3}$, for example are each a value equal to 0.5, when abs (AST_MOD2−AST_MOD1)≥0.5 Diopter and when abs(AST_AX2−AST_AX1)≥5°;

wherein "abs" means an absolute value;

(said rules have to be considered as a whole that allows choosing a, b, c, d parameter values for every possible astigmatism features (AST_MOD1, AST_MOD2, AST_AX1, AST_AX2) of an eye of a wearer);

the method further comprises a step where questions are asked to the wearer to determine his main visual task and the preferred viewing distance, PREFDIST, corresponding to said visual task, and wherein values of parameters a, b, c and d are chosen according to the preferred viewing distance, PREFDIST;

the method further comprises a step where visual acuity of the wearer is measured thanks to trial glasses, and wherein values of parameters a, b, c and d are chosen according to the wearer's visual acuity;

the method is implemented thanks to computer means.

the method comprises an optimization routine where at least a target of the optimization routine is the customized wearer's astigmatism features (AST_MOD_C, AST_AX_C);

the wearer's astigmatism features measured at the first proximity and/or the wearer's astigmatism features measured at the second proximity are measured in straight ahead gaze conditions;

the wearer's astigmatism features measured at the first proximity and/or the wearer's astigmatism features measured at the second proximity are measured in downward gaze conditions; according to an embodiment, measuring in downward gaze conditions is performed according to the method disclosed in patent application WO2008012299A2.

According to the present invention, far vision proximity relates to distances greater than 1 m, intermediate vision proximity relates to distances greater to 50 cm and equal or less than 1 m and near vision proximity relates to distances equal or greater to 20 cm and less than 50 cm. In the following, index "FV" refers to far vision, index "IV" refers to intermediate vision and index "NV" refers to near vision.

Calculating an ophthalmic lens for a wearer the by performing an optimization with a target lens uses optimization algorithms which are known by the one skilled in the art, for example disclosed in the publication "Application of optimization in computer-aided ophthalmic lens design" (P. Allione, F. Ahsbahs and G. Le Saux, in SPIE Vol. 3737, EUROPTO Conference on Design and Engineering of Optical Systems, Berlin, May 1999), which is incorporated by reference in the present document.

In still another aspect, the present invention relates to a computer program product comprising one or more stored sequence of instruction that is accessible to a processor and which, when executed by the processor, causes the processor to carry out at least one of the steps of the different embodiments of the preceding method when implemented by computer means.

The invention also relates to a computer-readable medium carrying one or more sequences of instructions of the preceding computer program product.

In still another aspect, the present invention relates to a method of manufacturing an ophthalmic lens comprising the step of surfacing at least a face of a lens blank so as the astigmatism features (AST_MOD, AST_AX) of the manufactured ophthalmic lens fulfil the astigmatism features calculated according to an embodiment of the here above recited method. According to an embodiment, the lens blank is a semi-finished lens blank comprising a finished front face and an unfinished back face and only the unfinished back face is surfaced. For progressive lenses, the semi-finished surface can be for example a front progressive surface having the optical design and the addition power selected for the wearer. Then, the unfinished back surface may be surfaced having a sphero-toric shape, so as to provide both spherical correction and cylindrical correction for the finished lens. The cylindrical correction provided by the back surface has the same value for the whole back surface of the lens, and is determined so that it provides the astigmatism feature (AST_MOD, AST_AX) according to the invention. This back surface can be obtained from free form surfacing devices, or from use of abrasion tools having sphero toric shape corresponding to the wanted shape of the unfinished back surface of the lens. As a consequence, contrary to the known art, the astigmatism correction is identical in far vision, near vision, and also all along the meridian line of the ophthalmic lens.

For single vision lenses, it may be possible for example to select the ophthalmic lens from a set of manufactured lens having different spherical power and cylindrical power. The ophthalmic lens is selected so that the ophthalmic lens spherical power and modulus of astigmatism correspond to wearer spherical power and astigmatism feature AST_MOD.

The lens can be then oriented when mounted on the frame so that the axis of astigmatism correspond to the AST_AX of the wearer.

In still another aspect, the present invention relates to a pair of spectacle lenses for a given wearer comprising two ophthalmic lenses where the astigmatism features (AST_MOD, AST_AX) of each ophthalmic lens of the pair are determined according to an embodiment of the here above recited method.

The inventors have performed a plurality of tests with a population of wearers; they have discovered that, when the wearer's needs refer to far vision and to near and/or intermediate vision(s) visual tasks, one can achieve excellent results for the wearers when choosing the values of parameters a, b, c and d according to following rules depending on AST_MOD1, AST_MOD2, AST_AX1, AST_AX2 values:

- a=c=0 and b=d=1, when abs(AST_MOD2−AST_MOD1) <0.5 Diopter and when abs(AST_AX2−AST_AX1)<5°;
- a=d=0 and c=b=1, when abs(AST_MOD2−AST_MOD1) <0.5 Diopter and when abs(AST_AX2−AST_AX1) ⩾ 5°;
- b=c=0 and a=d=1, when abs(AST_MOD2−AST_MOD1) ⩾ 0.5 Diopter and when abs(AST_AX2−AST_AX1)<5°;
- a, b, c and d values are each a value equal or less to $2/3$ and are each a value equal or greater to $1/3$, for example are each a value equal to 0.5, when abs(AST_MOD2−AST_MOD1) ⩾ 0.5 Diopter and when abs(AST_AX2−AST_AX1) ⩾ 5°.

Said rules allow choosing a, b, c, d parameter values for every possible astigmatism features (AST_MOD1, AST_MOD2, AST_AX1, AST_AX2) of an eye of a wearer. They have to be considered as a whole.

For this embodiment, and due to the fact that the wearer's needs refer to far vision and to near and/or intermediate vision(s) visual tasks, Prox1=Far vision proximity and Prox2=Near vision proximity or Prox2=Intermediate vision proximity.

The tests have been performed with a population of 22 people (44 eyes); the values of AST_MOD1, AST_MOD2, AST_AX1, AST_AX2 have been determined for each eye thanks to the Jackson Cross Cylinder test method (said method is well know from a person skilled in the art and uses a combination of two cylinders whose powers are numerically equal and of opposite sign (+/−) and whose axis are perpendicular to one another so as to measure astigmatism features of an eye). Visual comfort tests have been made for different visual corrections and for far vision and near and/or intermediate vision(s) visual tasks; the inventors have determined that the here above rules of choice for a, b, c, d parameter values were the ones that permit the most suitable improvement of visual comfort, for example of visual acuity, for the wearers when providing the wearer customized astigmatism correction (AST_MOD_C, AST_AX_C) for both the first proximity Prox1 and second proximity Prox2. The inventors have also discovered that using said rules was useful to avoid binocular imbalances or discomfort for the wearers. Satisfaction of the wearers was then significantly improved thanks to ophthalmic lenses according to these rules for far vision and to near and/or intermediate vision(s) visual tasks.

EXAMPLES

In the following examples, the first proximity Prox1 is the far vision proximity and the wearer's prescribed mean refractive power for the first proximity Prox1 is the prescribed sphere $SPH_p$, the wearer's astigmatism features measured at a first proximity Prox1 (AST_MOD1, AST_AX1) are respectively the prescribed astigmatism value $CYL_p$ and the prescribed axis $AXIS_p$, where said prescribed data are measured when the wearer is looking in a far vision gaze direction at a far distance. In said examples, the wearer's astigmatism features measured at the second proximity Prox2 (AST_MOD2, AST_AX2) are respectively the measured near vision astigmatism value $CYL_{NV}$ and the measured near vision axis $AXIS_{NV}$, where said data are measured when the wearer is looking in a near vision gaze direction at a near distance.

First set of examples (following examples 1 to 6) where the combination of the wearer's astigmatism features measured at the first proximity Prox1 and of the wearer's astigmatism features measured at the second proximity Prox2 results of following linear combinations:

AST_MOD_C=a·AST_MOD1+b·AST_MOD2;

AST_AX_C=c·AST_AX1+d·AST_AX2;

Parameters a, b, c and d are positive or nil values, each being equal or less to 1;

Parameter a value is different from 1 and/or parameter c value is different from 1;

a+b=1 and c+d=1.

According to a first embodiment (following examples 1 to 3) of these first set of examples:

a=c=0 and b=d=1, and:

AST_MOD_C=AST_MOD2;

AST_AX_C=AST_AX2;

Example 1

The ophthalmic lens is an ophthalmic single vision lens, and measurements made give following results: $SPH_p=-5D$, $CYL_p=-1D$ and $AXIS_p=10°$, $CYL_{NV}=-1.25D$, $AXIS_{NV}=13°$;

Here above and in the following, "D" refers to Diopter unit.

The customized wearer's astigmatism features are following:

SPH=−5D, AST_MOD_C=−1.25D and AST_AX_C=13°.

Example 2

The ophthalmic lens is a "plano" ophthalmic single vision lens, and measurements made give following results: $SPH_p=0D$, $CYL_p=0D$ and $AXIS_p=0°$, $CYL_{IV}=-0.25D$, $AXIS_{IV}=3°$;

The customized wearer's astigmatism features are following:

SPH=0D, AST_MOD_C=−0.25D and AST_AX_C=3°.

Example 3

The ophthalmic lens is an ophthalmic progressive addition lens, and measurements made give following results: $SPH_p=-5D$, $CYL_p=-1D$ and $AXIS_p=10°$, $ADD_p=2D$, $CYL_{NV}=-1.37D$, $AXIS_{NV}=7°$;

The customized wearer's astigmatism features are following:

In far vision: $SPH_{FV}=-5D$, $AST\_MOD\_C_{FV}=-1.37D$ and $AST\_AX\_C_{FV}=7°$.

In near vision: $SPH_{NV}=-3D$, $AST\_MOD\_C_{NV}=-1.37$ and $AST\_AX\_C_{NV}=7°$.

According to a second embodiment (following example 4) of these first set of examples:
a=d=0 and b=c=1, and:
AST_MOD_C=AST_MOD2;
AST_AX_C=AST_AX1;

Example 4

The ophthalmic lens is an ophthalmic single vision lens, and measurements made give following results: $SPH_p=-5D$, $CYL_p=-1D$ and $AXIS_p=10°$, $CYL_{NV}=-1.25D$, $AXIS_{NV}=18°$;
The customized wearer's astigmatism features are following:
SPH=-5D, AST_MOD_C=-1.25D and AST_AX_C=10°.
According to a third embodiment (following example 5) of these first set of examples:
b=c=0 and a=d=1, and:
AST_MOD_C=AST_MOD1;
AST_AX_C=AST_AX2;

Example 5

The ophthalmic lens is an ophthalmic single vision lens, and measurements made give following results: $SPH_p=-5D$, $CYL_p=-1D$ and $AXIS_p=10°$, $CYL_{NV}=-0.25$, $AXIS_{NV}=13°$;
The customized wearer's astigmatism features are following:
SPH=-5D, AST_MOD_C=-1D and AST_AX_C=13°.
According to a fourth embodiment (following example 6) of these first set of examples:
a=b=c=d=0.5, and:
AST_MOD_C=(AST_MOD1+AST_MOD2)/2;
AST_AX_C=(AST_AX1+AST_AX2)/2;

Example 6

The ophthalmic lens is an ophthalmic single vision lens, and measurements made give following results: $SPH_p=-5D$, $CYL_p=-1D$ and $AXIS_p=10°$, $CYL_{NV}=-2D$, $AXIS_{NV}=20°$;
The customized wearer's astigmatism features are following:
SPH=-5D, AST_MOD_C=-1.5D and AST_AX_C=15°.
Second set of examples where the combination of the wearer's astigmatism features measured at the first proximity Prox1 and of the wearer's astigmatism features measured at the second proximity Prox2 results of following linear combinations:
AST_MOD_C=a·AST_MOD1+b·AST_MOD2;
AST_AX_C=c·AST_AX1+d·AST_AX2;
One chooses the values of parameters a, b, c and d according to one of following CASE 1, CASE 2, CASE 3, CASE 4:
CASE 1: a=c=0 and b=d=1;
CASE 2: a=d=0 and b=c=1;
CASE 3: b=c=0 and a=d=1;
CASE 4: a=b=c=d=0.5;
The choice of CASE 1, CASE 2, CASE 3 and CASE 4 is made according to a set of rules as a function of the wearer's needs.
According to a first embodiment of these second set of examples, the wearer's needs refer to far vision and to near and/or intermediate vision(s) visual tasks and the set of rules corresponding to the wearer's needs is following:
CASE 1, when abs(AST_MOD2-AST_MOD1)<0.5 Diopter and when abs(AST_AX2-AST_AX1)<5°;
CASE 2, when abs(AST_MOD2-AST_MOD1)<0.5 Diopter and when abs(AST_AX2-AST_AX1)≥5°;
CASE 3, when abs(AST_MOD2-AST_MOD1)≥0.5 Diopter and when abs(AST_AX2-AST_AX1)<5°;
CASE 4, when abs(AST_MOD2-AST_MOD1)≥0.5 Diopter and when abs(AST_AX2-AST_AX1)≥5°.
According to a second embodiment of these second set of examples, set of rules as a function of the wearer's needs is following: the method further comprises a step where questions are asked to the wearer to determine his main visual task and the preferred viewing distance, PREFDIST, corresponding to said visual task, and the choice of parameter a,b,c and d is made according to the preferred viewing distance, PREFDIST.
According to an example related to said embodiment:
the wearer explains that he spends long time periods when looking at far distances and PREFDIST is defined as corresponding to a far vision visual task; choice of a>b and/or c>d recommended;
the wearer explains that he spends long time periods when looking at near distances and PREFDIST is defined as corresponding to a near vision visual task; one can choose b>a and/or d>c;
the wearer explains that he spends long time periods when looking at intermediate distances and PREFDIST is defined as corresponding to an intermediate vision visual task; one can choose a=b=0.5 and/or c=d=0.5.
According to a third embodiment of these second set of examples, set of rules as a function of the wearer's needs is following: the method further comprises a step where visual acuity of the wearer is measured thanks to trial glasses, and wherein values of parameters a, b, c and d are chosen according to the wearer's visual acuity. According to an example, visual acuity is measured in both far vision and near vision; According to another example, visual acuity is measured in both far vision and intermediate vision. This embodiment may be combined with previous one where questions are asked to the wearer to determine his main visual task and a preferred viewing distance, PREFDIST, corresponding to said visual task is determined. Parameters a, b, c, d are then determined so that global acuity, being the average acuity between far vision and near vision or far vision and intermediate vision, is maximized.
According to an embodiment, the method for providing an ophthalmic lens to a wearer according to the present invention comprises a sub-method for determining the wearer's astigmatism features, the sub-method comprising:
using a vision-compensating device allowing observation along an optical axis (X) of observation with an optical correction of variable power comprises a lens having, along the optical axis, a spherical power that is variable as a function of a first control, and an optical assembly generating, along the optical axis, a cylindrical correction that is variable as a function of at least one second control applied to said optical assembly; said vision-compensating device also comprises a module for receiving at least one setpoint for said optical correction and a module for determining the first control and the second control depending on said setpoint by means of a mode taking into account the distance (β2) separating said lens and said optical assembly.
The vision-compensating device, usually referred as a phoropter, used in said sub-method is disclosed in more details in PCT Application number WO2016FR51827, published as WO2017013343 (A1) ("VISION-COMPENSATING DEVICE, METHOD FOR CONTROLLING A VISION-COMPENSATING DEVICE AND BINOCULAR OPTOMETRY DEVICE"), which is hereby incorporated by reference.

Thanks to this sub-method, quick and accurate wearer's astigmatism features can be obtained.

According to an embodiment, the method for providing an ophthalmic lens to a wearer according to the present invention comprises a sub-method for determining a dioptric parameter corresponding to the wearer's astigmatism features, the sub-method comprising:

a set-up step, during which a test optical element having a dioptric function having a specific value of the dioptric parameter to be determined is provided to the person and the person is required to look at a visual target using the test optical element, a data collecting step, during which evaluation data and certitude data are collected, the evaluation data being indicative of the visual assessment expressed by the person looking at the visual target using the test optical element and certitude data being indicative of the degree of certainty of the person upon expressing the visual assessment, wherein the set-up and data collecting steps are repeated by varying the value of the dioptric parameter of the test optical element, and the method further comprises:

a global analyzing step, during which for each value of the dioptric parameter tested during the set-up and data collecting step a value a degree of certainty of the person is determined and the value of the dioptric parameter of the person is determined based on the values of degree of certainty of the person.

Said sub-method is disclosed in more details in EP application number 16305945.4, filed on 22 Jul. 2016, which is hereby incorporated by reference.

The present method can be implemented for providing numerous ophthalmic lenses types to a wearer, such as ophthalmic single vision lenses, multifocal lenses, such bifocal or trifocal ophthalmic lenses, ophthalmic progressive addition lenses, occupational lenses (intended to provide correct vision for both near and intermediate vision) or antifatigue lenses intended to provide correction vision for far vision and to provide small addition power for near or intermediate vision). Among ophthalmic progressive addition lenses, ophthalmic lenses may be suitable for far vision and intermediate vision and near vision (also called "standard ophthalmic progressive addition lenses), or for far vision and intermediate vision or for intermediate vision and near vision.

The invention claimed is:

1. A method for providing an ophthalmic lens to a wearer comprising:

providing wearer's astigmatism features measured at a first proximity, the wearer's astigmatism features comprising a modulus of astigmatism AST_MOD1 and an axis of astigmatism AST_AX1;

providing wearer's astigmatism features measured at a second proximity, the wearer's astigmatism features comprising a modulus of astigmatism AST_MOD2 and an axis of astigmatism AST_AX2, wherein the second proximity is greater than the first proximity;

determining customized astigmatism features (AST_MOD_C, AST_AX_C) based on a combination of the wearer's astigmatism features measured at the first proximity (AST_MOD1, AST_AX1) and of the wearer's astigmatism features measured at the second proximity (AST_MOD2, AST_AX2);

applying the customized astigmatism features (AST_MOD_C, AST_AX_C) to the ophthalmic lens to provide a wearer astigmatism correction (AST_MOD_C, AST_AX_C) for both the first proximity and second proximity;

wherein the combination of the wearer's astigmatism features measured at the first proximity and of the wearer's astigmatism features measured at the second proximity results of linear combinations wherein:

AST_MOD_C=a·AST_MOD1+b·AST_MOD2;
AST_AX_C=c·AST_AX1+d·AST_AX2;

parameters a, b, c and d are positive or nil values, each being equal or less to 1; parameter a value is different from 1 and/or parameter c value is different from 1; a+b=1 and c+d=1.

2. A method for providing an ophthalmic lens as claimed in claim 1, further comprising providing the wearer's prescribed mean refractive power for the first proximity.

3. A method for providing an ophthalmic lens as claimed in claim 1, wherein the lens is an ophthalmic single vision lens, and the customized astigmatism features (AST_MOD_C, AST_AX_C) are applied to the whole surface of the lens.

4. A method for providing an ophthalmic lens as claimed in claim 1, wherein the lens is an ophthalmic progressive addition lens, and the customized astigmatism features (AST_MOD_C, AST_AX_C) are applied to the meridian line of a target lens used to calculate by computer the ophthalmic lens for the wearer the by performing an optimization with the target lens.

5. A method for providing an ophthalmic lens as claimed in claim 1, wherein the first proximity Prox1 and the second proximity Prox2 are chosen within the list of (Prox1=Far vision proximity, Prox2=Near vision proximity); (Prox1=Far vision proximity, Prox2=Intermediate vision proximity); (Prox1=Intermediate vision proximity, Prox2=Near vision proximity).

6. A method for providing an ophthalmic lens as claimed in claim 5, wherein the first proximity is the far vision proximity.

7. A method for providing an ophthalmic lens as claimed in claim 6, wherein values of parameters a, b, c and d are chosen according to a set of rules as a function of needs of the wearers.

8. A method for providing an ophthalmic lens as claimed in claim 7, wherein the wearer's needs refer to far vision and to near and/or intermediate vision(s) visual tasks, and wherein values of parameters a, b, c and d are chosen according to following rules:

a=c=0 and b=d=1, when abs(AST_MOD2−AST_MOD1)<0.5 Diopter and when abs(AST_AX2−AST_AX1)<5°;

a=d=0 and c=b=1, when abs(AST_MOD2−AST_MOD1)<0.5 Diopter and when abs(AST_AX2−AST_AX1)≥5°;

b=c=0 and a=d=1, when abs(AST_MOD2−AST_MOD1)≥0.5 Diopter and when abs(AST_AX2−AST_AX1)<5";

a, b, c and d values are each a value equal or less to ⅔ and are each a value equal or greater to ⅓, for example are each a value equal to 0.5, when abs(AST_MOD2−AST_MOD1)≥0.5 Diopter and when abs(AST_AX2−AST_AX1)≥5°.

9. A method for providing an ophthalmic lens as claimed in claim 7, further comprising wherein questions are asked to the wearer to determine a main visual task and preferred viewing distance, PREFDIST, corresponding to the visual task, and wherein values of parameters a, b, c and d are chosen according to the preferred viewing distance, PREFDIST.

10. A method for providing an ophthalmic lens as claimed in claim 7, further comprising wherein visual acuity of the wearer is measured using trial glasses, and wherein values of parameters a, b, c and d are chosen according to the wearer's visual acuity.

11. A method for providing an ophthalmic lens as claimed in claim 1, implemented by a computer.

12. A method of manufacturing an ophthalmic lens comprising:

surfacing at least a face of a lens blank so as the astigmatism features (AST_MOD, AST_AX) of the manufactured ophthalmic lens fulfil the astigmatism features calculated according to claim 1.

13. A method of manufacturing an ophthalmic lens as claimed in claim 2, wherein the lens blank is a semi-finished lens blank comprising a finished front face and an unfinished back face and wherein only the unfinished back face is surfaced.

14. A pair of spectacle lenses for a given wearer comprising two ophthalmic lenses where the astigmatism features (AST_MOD, AST_AX) of each ophthalmic lens of the pair are determined according to the method of claim 1.

15. A method for providing an ophthalmic lens as claimed in claim 8, wherein the wearer's needs refer to far vision and to near and/or intermediate vision(s) visual tasks and where values of parameters a, b, c and d are chosen according to following rules:

- a=c=0 and b=d=1, when abs(AST_MOD2−AST_MOD1)<0.5 Diopter and when abs(AST_AX2−AST_AX1)<5°;
- a=d=0 and c=b=1, when abs(AST_MOD2−AST_MOD1)<0.5 Diopter and when abs(AST_AX2−AST_AX1)≥5°;
- b=c=0 and a=d=1, when abs(AST_MOD2−AST_MOD1)≥0.5 Diopter and when abs(AST_AX2−AST_AX1)<5°;
- a, b, c and d values are each a value equal to 0.5, when abs(AST_MOD2−AST_MOD1)≥0.5 Diopter and when abs(AST_AX2−AST_AX1)≥5°.

\* \* \* \* \*